US007258735B2

(12) United States Patent
Lin et al.

(10) Patent No.: US 7,258,735 B2
(45) Date of Patent: *Aug. 21, 2007

(54) PROCESS FOR AFFECTING THE SETTING AND WORKING TIME OF BIORESORBABLE CALCIUM PHOSPHATE CEMENTS

(75) Inventors: Jiin-Huey Chern Lin, Winnetka, IL (US); Chien-Ping Ju, Carbondale, IL (US); Kuan-Liang Lin, Tainan (TW); I-Chang Wang, Tainan (TW)

(73) Assignee: Calcitec, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/176,963

(22) Filed: Jul. 7, 2005

(65) Prior Publication Data

US 2006/0011099 A1    Jan. 19, 2006

Related U.S. Application Data

(63) Continuation of application No. 11/137,112, filed on May 25, 2005, which is a continuation of application No. 10/944,278, filed on Sep. 17, 2004, which is a continuation of application No. 10/328,019, filed on Dec. 26, 2002, now Pat. No. 6,840,995, which is a continuation-in-part of application No. 09/615,384, filed on Jul. 13, 2000, now abandoned, which is a continuation-in-part of application No. 09/351,912, filed on Jul. 14, 1999, now Pat. No. 6,379,453.

(51) Int. Cl.
*C04B 28/34* (2006.01)
(52) U.S. Cl. ...................................... 106/690; 106/691
(58) Field of Classification Search ............... 106/690, 106/691
See application file for complete search history.

(56) References Cited

U.S. PATENT DOCUMENTS

| | | | |
|---|---|---|---|
| 3,679,360 A | 7/1972 | Rubin et al. |
| 4,371,484 A | 2/1983 | Inukai et al. |
| 4,481,175 A | 11/1984 | Iino et al. |
| 4,518,430 A | 5/1985 | Brown et al. |
| 4,553,272 A | 11/1985 | Mears |
| 4,612,053 A | 9/1986 | Brown et al. |
| 4,623,553 A | 11/1986 | Ries et al. |
| RE33,161 E | 2/1990 | Brown et al. |
| RE33,221 E | 5/1990 | Brown et al. |
| 4,959,104 A | 9/1990 | Iino et al. |
| 5,017,518 A | 5/1991 | Hirayama et al. |
| 5,053,212 A | 10/1991 | Constantz et al. |
| 5,092,888 A | 3/1992 | Iwamoto et al. |
| 5,149,368 A | 9/1992 | Liu et al. |
| 5,152,791 A | 10/1992 | Hakamatsuka et al. |
| 5,164,187 A | 11/1992 | Constantz et al. |
| 5,180,426 A | 1/1993 | Sumita |
| 5,218,035 A | 6/1993 | Liu |
| 5,262,166 A | 11/1993 | Liu et al. |
| 5,336,264 A | 8/1994 | Constanz et al. |
| 5,338,356 A | 8/1994 | Hirano et al. |
| 5,342,441 A | 8/1994 | Mandai et al. |
| 5,409,982 A | 4/1995 | Imura et al. |
| 5,476,647 A | 12/1995 | Chow et al. |
| 5,492,768 A | 2/1996 | Okimatsu et al. |
| 5,496,399 A | 3/1996 | Ison et al. |
| 5,503,164 A | 4/1996 | Friedman |
| 5,522,893 A | 6/1996 | Chow et al. |
| 5,525,148 A | 6/1996 | Chow et al. |
| 5,536,575 A | 7/1996 | Imura et al. |
| 5,542,973 A | 8/1996 | Chow et al. |
| 5,545,254 A | 8/1996 | Chow et al. |
| 5,550,172 A | 8/1996 | Regula et al. |
| 5,569,490 A | 10/1996 | Imura et al. |
| 5,605,713 A | 2/1997 | Boltong |
| 5,607,685 A | 3/1997 | Cimbollek et al. |
| 5,652,016 A | 7/1997 | Imura et al. |
| 5,683,461 A | 11/1997 | Lee et al. |
| 5,683,496 A | 11/1997 | Ison et al. |

(Continued)

FOREIGN PATENT DOCUMENTS

EP    0267624    5/1988

(Continued)

OTHER PUBLICATIONS

PCT/US04/11637 International Search Report/Written Opinion, mailed Mar. 11, 2005, 5 pages.

(Continued)

*Primary Examiner*—C. Melissa Koslow
(74) *Attorney, Agent, or Firm*—Meyertons, Hood, Kivlin, Kowert & Goetzel, P.C.; Eric B. Meyertons

(57) ABSTRACT

A fast-setting, bioresorbable calcium phosphate cement is prepared by a process which can be carried out with a heat treatment up to 1000° C. on a mixture of a wetting solution and a calcium phosphate powder having a Ca to P molar ratio of 0.5-2.5. The wetting solution suitable for use in the process of the present invention includes water, an organic solvent, an acidic and basic solution. A setting solution for mixing with the heated powder to form the fast-setting, bioresorbable calcium phosphate cement may be water, an acidic or basic solution according to the process of the present invention.

18 Claims, No Drawings

U.S. PATENT DOCUMENTS

| | | | |
|---|---|---|---|
| 5,695,729 A | 12/1997 | Chow et al. |
| 5,697,981 A | 12/1997 | Ison et al. |
| 5,702,449 A | 12/1997 | McKay |
| 5,766,669 A | 6/1998 | Pugh et al. |
| 5,782,971 A | 7/1998 | Constantz et al. |
| 5,814,681 A | 9/1998 | Hino et al. |
| 5,820,632 A | 10/1998 | Constantz et al. |
| 5,846,312 A | 12/1998 | Ison et al. |
| 5,891,448 A | 4/1999 | Chow et al. |
| 5,899,939 A | 5/1999 | Boyce et al. |
| 5,954,867 A | 9/1999 | Chow et al. |
| 5,958,430 A | 9/1999 | Campbell et al. |
| 5,964,932 A | 10/1999 | Ison et al. |
| 5,976,234 A | 11/1999 | Chow et al. |
| 5,993,535 A | 11/1999 | Sawamura et al. |
| 5,997,624 A | 12/1999 | Chow et al. |
| 6,005,162 A | 12/1999 | Constantz |
| 6,013,591 A | 1/2000 | Ying et al. |
| 6,013,853 A | 1/2000 | Athanasiou et al. |
| 6,018,095 A | 1/2000 | Lerch et al. |
| 6,027,742 A | 2/2000 | Lee et al. |
| 6,077,989 A | 6/2000 | Kandel et al. |
| 6,083,229 A | 7/2000 | Constantz et al. |
| 6,117,456 A | 9/2000 | Lee et al. |
| 6,118,043 A | 9/2000 | Nies et al. |
| 6,123,731 A | 9/2000 | Boyce et al. |
| 6,132,463 A | 10/2000 | Lee et al. |
| 6,149,688 A | 11/2000 | Brosnahan et al. |
| 6,162,258 A | 12/2000 | Scarborough et al. |
| 6,277,149 B1 | 8/2001 | Boyle et al. |
| 6,294,041 B1 | 9/2001 | Boyce et al. |
| 6,294,187 B1 | 9/2001 | Boyce et al. |
| 6,323,146 B1 | 11/2001 | Pugh et al. |
| 6,325,987 B1 | 12/2001 | Sapieszko et al. |
| 6,325,992 B1 | 12/2001 | Chow et al. |
| 6,332,779 B1 | 12/2001 | Boyce et al. |
| 6,340,648 B1 | 1/2002 | Imura et al. |
| 6,379,453 B1 * | 4/2002 | Lin et al. ............. 106/690 |
| 6,440,444 B2 | 8/2002 | Boyce et al. |
| 6,458,162 B1 | 10/2002 | Koblish et al. |
| 6,478,825 B1 | 11/2002 | Winterbottom et al. |
| 6,495,156 B2 | 12/2002 | Wenz et al. |
| 6,530,955 B2 | 3/2003 | Boyle et al. |
| 6,533,821 B1 | 3/2003 | Lally |
| 6,547,866 B1 | 4/2003 | Edwards et al. |
| 6,569,489 B1 | 5/2003 | Li |
| 6,585,992 B2 | 7/2003 | Pugh et al. |
| 6,616,742 B2 | 9/2003 | Lin et al. |
| 6,648,960 B1 | 11/2003 | Lin et al. |
| 6,670,293 B2 | 12/2003 | Edwards et al. |
| 6,696,073 B2 | 2/2004 | Boyce et al. |
| 6,719,989 B1 | 4/2004 | Matsushima et al. |
| 6,730,129 B1 | 5/2004 | Hall et al. |
| 6,752,831 B2 | 6/2004 | Sybert et al. |
| 6,793,725 B2 | 9/2004 | Chow et al. |
| 6,808,561 B2 | 10/2004 | Genge et al. |
| 6,808,585 B2 | 10/2004 | Boyce et al. |
| 6,840,995 B2 * | 1/2005 | Lin et al. ............. 106/690 |
| 6,960,249 B2 | 11/2005 | Lin et al. |
| 6,994,726 B2 | 2/2006 | Lin et al. |
| 2002/0019635 A1 | 2/2002 | Wenstrom, Jr. et al. |
| 2002/0073894 A1 | 6/2002 | Genge et al. |
| 2002/0137812 A1 | 9/2002 | Chow et al. |
| 2002/0169066 A1 | 11/2002 | Cassidy et al. |
| 2003/0019396 A1 | 1/2003 | Edwards et al. |
| 2003/0021824 A1 | 1/2003 | Lacout et al. |
| 2003/0031698 A1 | 2/2003 | Roeder et al. |
| 2003/0039676 A1 | 2/2003 | Boyce et al. |
| 2003/0055512 A1 | 3/2003 | Genin et al. |
| 2003/0074081 A1 | 4/2003 | Ayers et al. |
| 2003/0078317 A1 | 4/2003 | Lin et al. |
| 2003/0120351 A1 | 6/2003 | Tofighi |
| 2003/0121450 A1 | 7/2003 | Lin et al. |
| 2003/0167093 A1 | 9/2003 | Xu et al. |
| 2003/0216777 A1 | 11/2003 | Tien et al. |
| 2004/0003757 A1 | 1/2004 | Chern Lin et al. |
| 2004/0022825 A1 | 2/2004 | Lagow |
| 2004/0031420 A1 | 2/2004 | Lin et al. |
| 2004/0076685 A1 | 4/2004 | Tas |
| 2004/0137032 A1 | 7/2004 | Wang |
| 2004/0175320 A1 | 9/2004 | Lin et al. |
| 2004/0180091 A1 | 9/2004 | Lin |
| 2004/0185181 A1 | 9/2004 | Matsumoto |
| 2004/0186481 A1 | 9/2004 | Chern Lin et al. |
| 2005/0008759 A1 | 1/2005 | Nie et al. |
| 2005/0029701 A1 | 2/2005 | Lin et al. |
| 2005/0069479 A1 | 3/2005 | Lin et al. |
| 2005/0076813 A1 | 4/2005 | Lin et al. |
| 2005/0101964 A1 | 5/2005 | Lin et al. |
| 2005/0184417 A1 | 8/2005 | Chern Lin et al. |
| 2005/0184418 A1 | 8/2005 | Lin et al. |
| 2005/0186353 A1 | 8/2005 | Lin et al. |
| 2005/0186354 A1 | 8/2005 | Lin et al. |
| 2005/0186449 A1 | 8/2005 | Lin et al. |
| 2005/0263919 A1 | 12/2005 | Lin et al. |
| 2005/0263920 A1 | 12/2005 | Lin et al. |
| 2005/0263921 A1 | 12/2005 | Lin et al. |
| 2005/0263922 A1 | 12/2005 | Lin et al. |
| 2005/0263927 A1 | 12/2005 | Lin et al. |
| 2005/0263928 A1 | 12/2005 | Lin et al. |
| 2005/0263929 A1 | 12/2005 | Lin et al. |
| 2005/0263930 A1 | 12/2005 | Lin et al. |
| 2005/0263931 A1 | 12/2005 | Lin et al. |
| 2005/0267587 A1 | 12/2005 | Lin et al. |
| 2005/0267588 A1 | 12/2005 | Lin et al. |
| 2005/0267589 A1 | 12/2005 | Lin et al. |
| 2005/0267593 A1 | 12/2005 | Lin et al. |
| 2005/0267604 A1 | 12/2005 | Lin et al. |
| 2005/0268819 A1 | 12/2005 | Lin et al. |
| 2005/0268820 A1 | 12/2005 | Lin et al. |
| 2005/0268821 A1 | 12/2005 | Lin et al. |
| 2005/0271740 A1 | 12/2005 | Lin et al. |
| 2005/0271741 A1 | 12/2005 | Lin et al. |
| 2005/0271742 A1 | 12/2005 | Lin et al. |
| 2005/0274282 A1 | 12/2005 | Lin et al. |
| 2005/0274286 A1 | 12/2005 | Lin et al. |
| 2005/0274287 A1 | 12/2005 | Lin et al. |
| 2005/0274288 A1 | 12/2005 | Lin et al. |
| 2005/0274289 A1 | 12/2005 | Lin et al. |
| 2005/0279252 A1 | 12/2005 | Lin et al. |
| 2005/0279256 A1 | 12/2005 | Lin et al. |
| 2006/0011099 A1 | 1/2006 | Lin et al. |

FOREIGN PATENT DOCUMENTS

| | | |
|---|---|---|
| JP | 06-228011 | 8/1994 |
| WO | WO 03/055418 | 7/2003 |

OTHER PUBLICATIONS

Sugawara et al., "Calcium Phosphate Cement: An In Vitro Study of Dentin Hypersensitivity Using Calcium Phosphate Cement", The Journal of the Japanese Society for Dental Materials and Devices, 1989, vol. 8, pp. 282-294.

Pickel et al., "The Effects of a Chewing Gum Containing Dicalcium Phosphate on Salivary Calcium and Phosphate", Ala. J. Med. Sci., 1965, vol. 2, pp. 286-287.

Matsuya et al., "Effects of pH on the Reactions of Tetracalcium Phosphate and Dicalcium Phosphate", IADR Abstact, Apr. 1991.

Sugawara et al., "Formation of Hydroxyapatite in Hydrogels from Tetracalcium Phosphate/Dicalcium Phosphate Mixtures," J. Nihon. Univ. Sch. Dent., 1989, vol. 31, pp. 372-381.

Hong et al., "The Periapical Tissue Reactions to a Calcium Phosphate Cement in the Teeth of Monkeys," J. Biomed. Mater. Res., Apr. 1991, vol. 25(4), pp. 485-498.

de Rijk, et al., "Clinical Evaluation of a Hydroxyapatite Precipitate for the Treatment of Dentinal Hypersensitivity," Biomedical Engineering v. Recent Developments, Proc. of 5th Southern Biomedical Engineering Conference, 1986, pp. 336-339. (Pergamon Press, New York).

Gruninger et al., "Evaluation of the Biocompatibility of a New Calcium Phosphate Setting Cement," J. Dent. Res., 1984, 63, Abst. No. 270 (4 pages).

Costantino et al., "Evaluation of a New Hydroxyapatite Cement: Part III: Cranioplasty in a Cat Model," The Fifth Intl. Symposium on Facial Plastic Reconstructive Surgery of the Head and Neck, Toronto, Canada, 1989. (18 pages).

Shindo, et al., "Facial Skeletal Augmentation Using Hydroxyapatite Cement," Arch. Otolaryngol. Head Neck Surg., 1993, vol. 119, pp. 185-190.

Briner et al., "Significance of Enamel Remineralization", J. Dent. Res., 1974, vol. 53, pp. 239-243.

Silverstone L.M., "Remineralization Phenomena", Caries Res., 1977, vol. 11 (Supp. 1), pp. 59-84.

Costantino et al., "Hydroxyapatite Cement: I. Basic Chemistry and Histologic Properties," Arch. Otolaryngol. Head Neck Surg., 1991, vol. 117, pp. 379-394.

Friedman et al., "Hydroxyapatite Cement: II. Obliteration and Reconstruction of the Cat Frontal Sinus," Arch. Otolaryngol. Head Neck Surg., 1991, vol. 117, pp. 385-389.

Costantino et al., "Experimental Hydroxyapatite Cement Cranioplasty," Plast. Reconstr. Surg., 1992, vol. 90, No. 2, pp. 174-185.

Miyazaki et al., "An Infrared Spectroscopic Study of Cement Formation of Polymeric Calcium Phosphate Cement," The Journal of the Japanese Society for Dental Materials and Devices, 1992, vol. 11, No. 2, pp. 278-284.

Driskell et al., "Development of Ceramic and Ceramic Composite Devices for Maxillofacial Applications", J. Biomed. Mater. Res. Symposium, 1972, vol. 6, No. 2 (part 2), pp. 345-361.

Hiatt et al., "Root Preparation I. Obturation of Dentinal Tubules in Treatment of Root Hypersensitivity", J. Periodontol., 1972, vol. 41, No. 6, pp. 373-380.

Patel et al., "Solubility of $CaHPO_4$ $2H_2O$ in the Quaternary System $Ca(OH)_2$-$H_3PO_4$-NaCl-$H_2O$ at 25° C.," J. Res. Nat. Bur. Stand. (Physics Chem.), 1974, vol. 78A, pp. 675-681.

Salyer et al., "Porous Hydroxyapatite as an Onlay Bone-Graft Substitute for Maxillofacial Surgery," Presented at the 54th Annual Scientific Meeting of the American Society of Plastic and Reconstructive Surgeons, Kansas City, Missouri, 1985, pp. 236-244.

Kenney et al., "The Use of a Porous Hydroxylapatite Implant in Periodontal Defects: II. Treatment of Class II Furcation Lesions in Lower Molars," J. Periodontol, 1988, pp. 67-72.

Zide et al., "Hydroxylapatite Cranioplasty Directly Over Dura," J. Oral Maxillofac. Surg., 1987, vol. 45, pp. 481-486.

Waite et al., "Zygomatic Augmentation with Hydroxylapatite: A Preliminary Report," J. Oral Maxillofac. Surg., 1986, pp. 349-352.

Verwoerd, et al. Porous Hydroxyapatite-perichondrium Graft in Cricoid Reconstruction, Acta Otolaryngol., 1987, vol. 103, pp. 496-502.

Grote, "Tympanoplasty With Calcium Phosphate," Arch. Otolaryngol., 1984, vol. 110, pp. 197-199.

Kent et al., "Alveolar Ridge Augmentation Using Nonresorbable Hydroxylapatite with or without Autogenous Cancellous Bone," J. Oral Maxillofac. Surg., 1983, vol. 41, pp. 629-642.

Piecuch, J.F., "Augmentation of the Atrophic Edentulous Ridge with Porous Replamineform Hydroxyapatite (Interpore-200)", Dental Clinics of North America, 1986, vol. 30(2), pp. 291-305.

Misch, C.E., "Maxillary Sinus Augmentation for Endosteal Implants: Organized Alternative Treatment Plans," Int. J. Oral. Implant., 1987, vol. 4(2), pp. 49-58.

Chohayeb, et al., "Evaluation of Calcium Phosphate as a Root Canal Sealer-Filler Material," J. Endod., 1987, vol. 13, pp. 384-386.

Brown et al., "Crystallography of Tetracalcium Phosphate," J. Res. Nat. Bur. Stand. (Physics Chem.), 1965, vol. 69A, pp. 547-551.

Sanin et al., "Particle Size Effects on pH and Strength of Calcium Phosphate Cement," IADR Abstract, Apr. 1991.

Chow et al., "X-ray Diffraction and Electron Microscopic Characterization of Calcium Phosphate Cement Setting Reactions," IADR Abstract, 1987.

Block et al. "Correction of Vertical Orbital Dystopia with a Hydroxylapatite Orbital Floor Graft," J. Oral Maxillofac. Surg., 1988, vol. 46, pp. 420-425.

Brown, W.E., "Solubilities of Phosphates and Other Sparingly Soluble Compounds", Environmental Phosphorous Handbook, 1973, pp. 203-239. (John Wiley & Sons, New York).

Gregory et al., "Solubility of $CaHPO_4$ $2H_2O$ in the System $Ca(OH)_2$-$H_3PO_4$-$H_2O$ at 5, 15, 25, and 37.5° C.," J. Res. Nat. Bur. Stand. (Physics Chem.), 1970, vol. 74A, No. 4, pp. 461-475.

Gregory et al., "Solubility of β -$Ca_3(PO_4)_2$ in the System $Ca(OH)_2$-$H_3PO_4$-$H_2O$ at 5, 15, 25 and 37° C.," J. Res. Nat. Bur. Stand. (Physics Chem.), 1974, vol. 78A, No. 6, pp. 667-674.

McDowell et al., "Solubility of $Ca_5(PO_4)_3OH$ in the System $Ca(OH)_2$-$H_3PO_4$-$H_2O$ at 5, 15, 25 and 37° C.," J. Res. Nat. Bur. Stand. (Physics Chem.), 1977, vol. 91A, Nos. 2 and 3, pp. 273-281.

McDowell et al., "Solubility Study of Calcium Hydrogen Phosphate. Ion Pair Formation," Inorg. Chem., 1971, vol. 10, pp. 1638-1643.

Moreno et al., "Stability of Dicalcium Phosphate Dihydrate in Aqueous Solutions and Solubility of Octocalcium Phosphate," Proc. Soil Sci. Soc. Am., 1960, vol. 21, pp. 99-102.

Chow et al, "Self-Setting Calcium Phosphate Cements," Mat. Res. Soc. Symp. Proc., vol. 179, 1991, pp. 3-23.

Miyazaki et al., "Chemical Change of Hardened PCA/CPC Cements in Various Storing Solutions", The Journal of the Japanese Society for Dental Materials and Devices, 1992, vol. 11, No. 2, pp. 324-330.

Fukase et al, "Thermal Conductivity of Calcium Phosphate Cement", IADR Abstract, Mar. 1990.

Sugawara et al., "Biocompatibility and Osteoconductivity of Calcium Phosphate Cement", IADR Abstract, Mar. 1990.

Miyazaki et al., "Polymeric Calcium Phosphate Cements", IADR Abstract, Mar. 1990.

Link et al., "Composite of Calcium Phosphate Cement and Genetically Engineered Protein Bioadhesive," IADR Abstract, Mar. 1991.

Chow, "Development of Self-Setting Calcium Phosphate Cements", Journal of The Ceramic Society of Japan, 1991, vol. 99 [10], pp. 954-964.

Brown et al., A New Calcium Phosphate, Water Setting Cement, Cements Research Progress 1986, P.W. Brown, Ed., Westerville, Ohio: American Ceramic Society, 1988, pp. 352-379.

Sugawara et al., "A Calcium Phosphate Root Canal Sealer-Filler" IADR Abstract, 1987.

Sugawara et al., "In Vitro Evaluation of the Sealing Ability of a Calcium Phosphate Cement When Used as a Root Canal Sealer-Filler," J. Endodon., 1990, vol. 16, No. 4, pp. 162-165.

Chow, L.C., "Calcium Phosphate Materials: Reactor Response," Adv. Dent. Res., 1988, vol. 2(1), pp. 181-184.

Fukase et al., "Setting Reactions and Compressive Strengths of Calcium Phosphate Cements", J. Dent. Res., 1990, vol. 69(12), pp. 1852-1856.

Miyazaki et al., "Cements," Guide to Dental Materials and Devices, 7th Edition, 1974-1975, Chapter 6.

Sugawara et al., "Formation of Hydroxyapatite in Hydrogels from Tetracalcium Phosphate/Dicalcium Phosphate Mixtures," J. Nihon Univ. Sch. Dent., vol. 31, 372-381, 1989.

Chow et al. "A Natural Bone Cement-A Laboratory Novelty Led to the Development of Revolutionary New Biomaterials", J. Res. Natl. Inst. Stand. Technol., 2001, vol. 106, pp. 1029-1033.

Gbürek et al., "Mechanical Activation of Tetracalcium Phsophate," J. Am. Ceramics Soc., vol. 87(2), pp. 311-313.

Office communication for U.S. Appl. No. 10/773,701, mailed Jan. 5, 2006.

Office communication for U.S. Appl. No. 11/133,165, mailed Jan. 6, 2006.

Office communication for U.S. Appl. No. 11/133,152, mailed Nov. 15, 2005.

* cited by examiner

PROCESS FOR AFFECTING THE SETTING AND WORKING TIME OF BIORESORBABLE CALCIUM PHOSPHATE CEMENTS

CROSS-REFERENCE TO RELATED APPLICATION(S)

This is a continuation of and claims the benefit of priority under 35 USC § 120 to U.S. patent application Ser. No. 11/137,112, filed May 25, 2005, which is a continuation of U.S. patent application Ser. No. 10/944,278, filed Sep. 17, 2004, which is a continuation of U.S. patent application Ser. No. 10/328,019, filed Dec. 26, 2002, now U.S. Pat. No. 6,840,995, which is a continuation-in-part application of U.S. patent application Ser. No. 09/615,384, filed Jul. 13, 2000, now abandoned, which is a continuation-in-part application of U.S. patent application Ser. No. 09/351,912, filed Jul. 14, 1999, now U.S. Pat. No. 6,379,453B1. The above-listed applications are commonly assigned with the present invention and the entire contents of which are incorporated herein by reference.

BACKGROUND OF THE INVENTION

1. Field of the Invention

The present invention relates to a process for producing fast-setting, bioresorbable calcium phosphate cements (CPC), and in particular, to a process including a pre-heat treatment step to generate whiskers or fine crystals on surfaces of the CPC particles.

2. Description of the Related Art

U.S. Pat. No. 6,379,453B1 which is commonly assigned with the present invention discloses a process for producing a fast-setting, bioresorbable calcium phosphate cement comprising the following steps: obtaining a powder mixture from at least one calcium phosphate selected from the group consisting of $Ca_4(PO_4)_2O$, $CaHPO_4 \cdot 2H_2O$, $CaHPO_4$, $Ca_8H_2(PO_4)_6 \cdot 5H_2O$, alpha-$Ca_3(PO_4)_2$, beta-$Ca_3(PO_4)_2$, $Ca_2P_2O_7$, $Ca_2P_2O$, wherein the molar ratio of Ca to P in the mixture is roughly between 1 and 2; mixing the powder mixture in a phosphate-containing solution to obtain a powder/solution mixture having a concentration of less than 4 g powder mixture per ml solution; immediately heating the powder/solution mixture to a temperature of roughly 50° C. to 350° C. to obtain a powder containing uniformly distributed submicron-sized apatite crystals; and mixing the apatite crystal-containing powder in a phosphate ion-containing solution to obtain a fast-setting, bioresorbable calcium phosphate cement.

SUMMARY OF THE INVENTION

An extensive study on the preparation of the fast-setting, bioresorbable calcium phosphate cement disclosed in U.S. Pat. No. 6,379,453B1 has been conducted by the same inventors and their co-workers, and found that the fast-setting, bioresorbable calcium phosphate cement can be prepared under various conditions. Therefore an object of the invention is to provide a more comprehensive process for producing a fast-setting, bioresorbable calcium phosphate cement.

The invention accomplishes the above object by providing a process which can be carried out with a heat treatment up to 1000° C. on a mixture of a wetting solution and a calcium phosphate powder having a Ca to P molar ratio of 0.5-2.5. The wetting solution suitable for use in the process of the present invention includes water, an organic solvent, an acidic and basic solution, not limited to the phosphate-containing solution. A setting solution for mixing with the heated powder to form the fast-setting, bioresorbable calcium phosphate cement may be an acidic solution, a basic solution or substantially pure water according to the process of the present invention.

DETAILED DESCRIPTION OF THE INVENTION

The preferred embodiments of the present invention include (but not limited to) the following:

1) A process for producing a fast-setting, bioresorbable calcium phosphate cement, comprising the following steps:

(a) obtaining a calcium phosphate powder comprising at least one calcium phosphate selected from the group consisting of $Ca_4(PO_4)_2O$, $CaHPO_4 \cdot 2H_2O$, $CaHPO_4$, $Ca_8H_2(PO_4)_6 \cdot 5H_2O$, alpha-$Ca_3(PO_4)_2$, beta-$Ca_3(PO_4)_2$, $Ca_2P_2O_7$, $Ca_2H_2P_2O_8$, wherein the molar ratio of Ca to P in said calcium phosphate powder is between about 0.5 and 2.5;

(b) mixing said calcium phosphate powder obtained from step (a) with a wetting solution to obtain a powder/solution mixture in a ratio of less than about 10 g powder per ml solution;

(c) heating the powder/solution mixture resulting from step (b) to a temperature up to about 1000° C. and (d) mixing the resulting dried powder from step (c) in a setting solution to obtain the fast-setting, bioresorbable calcium phosphate cement.

2) The process as set forth in item 1), wherein said Ca/P molar ratio in step (a) is between 1.0 and 2.0.

3) The process as set forth in item 2), wherein in step (d) the resulting dried powder from step (c) together with at least one additive selected from the group of sodium phosphate ($Na_3PO_4$), disodium hydrogen phosphate ($Na_2HPO_4$), sodium dihydrogen phosphate ($NaH_2PO_4$), disodium hydrogen phosphate dodecahydrate ($Na_2HPO_4 \cdot 12H_2O$), disodium hydrogen phosphate heptahydrate ($Na_2HPO_4 \cdot 7H_2O$), sodium phosphate dodecahydrate ($Na_3PO_4 \cdot 12H_2O$), orthophosphoric acid ($H_3PO_4$), calcium sulfate ($CaSO_4$), $Ca_4(PO_4)_2O$, $CaHPO_4 \cdot 2H_2O$, $CaHPO_4$, $Ca_8H_2(PO_4)_6 \cdot 5H_2O$, alpha-$Ca_3(PO_4)_2$, beta-$Ca_3(PO_4)_2$, $Ca_2P_2O_7$, and $Ca_2H_2P_2O_8$, are mixed with the setting solution to obtain the fast-setting, bioresorbable calcium phosphate cement.

4) The process as set forth in item 3), wherein said wetting solution in step (b) is an acidic aqueous solution, a basic aqueous solution, an organic solvent, or substantially pure water.

5) The process as set forth in item 4), wherein the organic solvent is ethanol.

6) The process as set forth in item 1), wherein the mixing ratio in step (b) is less than about 5 g powder per ml solution.

7) The process as set forth in item 1), wherein the heating temperature in step (c) is up to about 500° C.

8) The process as set forth in item 1), wherein the setting solution in step (d) is an acidic aqueous solution, a basic aqueous solution, or a substantially pure water.

9) The process as set forth in item 4) or 8), wherein the acidic aqueous solution is selected from the group consisting of nitric acid ($HNO_3$), hydrochloric acid (HCl), phosphoric acid ($H_3PO_4$), carbonic acid ($H_2CO_3$), sodium dihydrogen phosphate ($NaH_2PO_4$), sodium dihydrogen phosphate monohydrate, sodium dihydrogen phosphate dihydrate, potassium dihydrogen phosphate ($KH_2PO_4$), ammonium dihydrogen phosphate ($NH_4H_2PO_4$), malic acid, acetic acid, lactic acid, citric acid, malonic acid, succinic acid, glutaric acid, tartaric acid, oxalic acid and their mixture.

10) The process as set forth in item 4) or 8), wherein the basic aqueous solution is selected from the group consisting of ammonia, ammonium hydroxide, alkali metal hydroxide, alkali earth hydroxide, disodium hydrogen phosphate ($Na_2HPO_4$), disodium hydrogen phosphate dodecahydrate, disodium hydrogen phosphate heptahydrate, sodium phosphate dodecahydrate ($Na_3PO_4.12H_2O$), dipotassium hydrogen phosphate ($K_2HPO_4$), potassium phosphate tribasic ($K_3PO_4$), diammonium hydrogen phosphate (($NH_4)_2HPO_4$), ammonium phosphate trihydrate (($NH_4)_3PO_4.3H_2O$), sodium bicarbonate ($NaHCO_3$), and their mixture.

11) The process as set forth in item 1) further comprising grinding the resulting dried powder from step (c) between step (c) and step (d).

12) The process as set forth in item 1), wherein the fast-setting, bioresorbable calcium phosphate cement obtained from step (d) has a viscosity so that it can be injected by a syringe.

The following examples are intended to demonstrate the invention more fully without acting as a limitation upon its scope, since numerous modifications and variations will be apparent to those skilled in this art.

EXAMPLE 1

To fabricate the CPC, the TTCP ($Ca_4(PO_4)_2O$) powder was prepared from the reaction of dicalcium pyrophosphate ($Ca_2P_2O_7$) (Sigma Chem. Co., St Louis, Mo., USA) and calcium carbonate ($CaCO_3$) (Katayama Chem. Co., Tokyo, Japan) using the method suggested by Brown and Epstein [Journal of Research of the National Bureau of Standards—A Physics and Chemistry 6 (1965) 69A 12], while the DCPA ($CaHPO.sub.4$) powder is a commercial product (Jassen Chemical Co., Japan).

5 g of a mixed powder of DCPA and TTCP in 1:1 molar ratio and 1.6 ml of a wetting solution of a phosphoric acid aqueous solution having a pH of 1.96 were mixed, and stirred for one minute. The resulting mixture was placed into an oven at 50° C. for 15 minutes, and the resulting dried mixture was mechanically ground for 20 minutes to fine particles after being removed from the oven. 1 g of the fine particles and 0.4 ml of phosphate aqueous solution (1.0 M, pH=6.0) were mixed to form a paste, which was tested every 30 seconds to determine the working time and the setting time. The setting time is the time required when a 1 mm diameter pin with a load of ¼ pounds can be inserted only 1 mm deep into the surface of the paste. The working time is the time after which the paste is too viscous to be stirred. The working time of the paste of this example is 6.5 minutes and the setting time thereof is 11.5 minutes.

The paste was placed in a relatively large amount of deionized water immediately following the formation thereof, and it was observed that the paste was non-dispersive in deionized water.

EXAMPLES 2-5

The procedures of Example 1 were repeated except that the heat treatment at 50° C. for 15 minutes was changed according to the conditions listed in Table 1. The performance is also listed in Table 1.

TABLE 1

| | Controlling treatment | Setting/working time (min) | Dispersive in water |
|---|---|---|---|
| Ex. 1 | Heating, 50° C. | 11.5/6.5 | No |
| Ex. 2 | Heating, 100° C. | 13.5/8.0 | No |
| Ex. 3 | Heating, 150° C. | 8.5/8.0 | No |
| Ex. 4 | Heating, 500° C. | 2.5/1.5 | No |
| Ex. 5 | Heating, 1000° C. | 35/31 | No |

EXAMPLES 6-10

The procedures of Example 1 were repeated by using the calcium phosphate powders and the wetting solutions listed in Table 2. The performance is also listed in Table 2.

TABLE 2

| | Calcium phosphate powder | Wetting solution | Setting/working time (min) | Dispersive in water |
|---|---|---|---|---|
| Ex. 6 | TCP | Phosphoric acid | 10/6.5 | No |
| Ex. 7 | TCP | Ethanol | 12.5/8.5 | No |
| Ex. 8 | TTCP + DCPA | Phosphoric acid | 11/8 | No |
| Ex. 9 | TTCP + DCPA + TCP | Phosphoric acid | — | No |
| Ex. 10 | DCPA + TCP | Phosphoric acid | 29/24 | No |

EXAMPLES 11-22

The procedures of Example 1 were repeated by using the wetting solutions having different pH values listed in Table 3. The performance is also listed in Table 3.

TABLE 3

| | Wetting solution | pH | Dispersive in water |
|---|---|---|---|
| Ex. 11 | Phosphoric acid | 0.56 | No |
| Ex. 12 | Phosphoric acid | 1.03 | No |
| Ex. 13 | Phosphoric acid | 1.17 | No |
| Ex. 14 | Phosphoric acid | 1.22 | No |
| Ex. 15 | Phosphoric acid | 1.32 | No |
| Ex. 16 | Phosphoric acid | 2.0 | No |
| Ex. 17 | Acetic acid + sodium carbonate | 7.0 | No |
| Ex. 18 | Sodium hydroxide | 9.5 | No |
| Ex. 19 | Sodium hydroxide | 12.55 | No |
| Ex. 20 | Acetic acid | 1.96 | No |
| Ex. 21 | Ethanol | — | No |
| Ex. 22 | Deionized water | 7.0 | No |

In the following examples, different setting solutions were used to verify the effect of the setting solution on the non-dispersive property of the calcium phosphate cement.

EXAMPLES 23-30

5 g of a mixed powder of DCPA and TTCP in 1:1 molar ratio and 1.6 ml of a wetting solution of 25 mM phosphoric acid aqueous solution were mixed, and stirred for one minute. The resulting mixture was placed into an oven at 50° C. for 15 minutes, and the resulting dried mixture was mechanically ground for 20 minutes to fine particles after being removed from the oven. 1 g of the fine particles and 0.4 ml of the setting solutions listed in Table 4 were mixed to form a past, which was tested every 30 seconds to determine the working time and the setting time as defined in Example 1. The results are shown in Table 4.

EXAMPLES 31-33

The procedures of Example 23 were repeated except that an additive as shown in Table 4 was added to the mixed powder of DCPA and TTCP in a weight ratio of 1:10 after the mixed powder was removed from the oven, and the setting solution used in these examples was deionized water. The results are shown in Table 4.

EXAMPLES 34-45

To 5 g TTCP powder which was used as synthesized 10 ml of 1M phosphoric acid aqueous solution was poured, and the mixture was filtered immediately. The filtered cake was placed into an oven at 150° C. for 10 minutes, and the resulting dried mixture was mechanically ground for 5 hours to fine particles. The resulting heat-treated TTCP fine particles and the TTCP powder as synthesized (without heat treatment) were mixed in a weight ratio of 1:1.1 g of the mixed TTCP powder and 0.4 ml of the setting solutions listed in Table 4 were mixed to form a paste, which was tested every 30 seconds to determine the working time and the setting time as defined in Example 1. The results are shown in Table 4.

What is claimed is:

1. A method of making a calcium phosphate cement (CPC) paste having either a desired setting time or a desired working time, the method comprising:
   contacting a calcium phosphate powder comprising one or more calcium phosphates with a wetting solution to form a mixture, the calcium phosphate powder having a Ca/P molar ratio in the range of 0.5-2.5;
   drying the mixture by heating the mixture at a temperature of up to about 1000° C.;
   forming calcium phosphate cement particles from the heated mixture; and
   contacting the calcium phosphate cement particles with a sufficient volume of a setting solution to form an injectable paste;
   wherein one or more of the calcium phosphates, the wetting solution, the setting solution, and the temperature that the mixture is heated to is selected such that the injectable paste has either a setting time in the range of 2.5 min to 35 min or a working time in the range of 1.5 min to 31 min.

2. The method of claim 1, wherein the calcium phosphates, the setting solution and the temperature that the mixture are heated to is selected such that the injectable paste has a setting time in the range of 10 min to 29 min.

3. The method of claim 1, wherein the temperature that the mixture is heated to is less than about 500° C.

TABLE 4

| | Powder | Setting solution | pH | Dispersive in water | Setting time/working time (min) |
|---|---|---|---|---|---|
| Ex. 23 | TTCP + DCPA | 25 mM $H_3PO_4$ | 1.96 | No | |
| Ex. 24 | TTCP + DCPA | Acetic acid | | No | |
| Ex. 25 | TTCP + DCPA | $HNO_3$ | | No | |
| Ex. 26 | TTCP + DCPA | HCl | | No | |
| Ex. 27 | TTCP + DCPA | $(NH4)HPO_4$ | 7.96 | No | 13.0/8.0 |
| Ex. 28 | TTCP + DCPA | $K_2HPO_4$ | 8.76 | No | 31.0/23.5 |
| Ex. 29 | TTCP + DCPA | NaOH | 13.57 | No | 28.0/19.0 |
| Ex. 30 | TTCP + DCPA | Deionized water | 7.0 | No | |
| Ex. 31 | TTCP + DCPA + phosphoric acid | Deionized water | 7.0 | No | |
| Ex. 32 | TTCP + DCPA + $NaH_2PO_4.2H_2O$ | Deionized water | 7.0 | No | 20.5/16.5 |
| Ex. 33 | TTCP + DCPA + $Na_2HPO_4.2H_2O$ | Deionized water | 7.0 | No | 11.0/7.0 |
| Ex. 34 | TTCP | Deionized water | 7.0 | No | 35.0/31.0 |
| Ex. 35 | TTCP | 3M $H_3PO_4$ | −0.7 | No | 17.5/16.0 |
| Ex. 36 | TTCP | HCl | −1.53 | No | |
| Ex. 37 | TTCP | HCl | −0.83 | No | 22.5/17.5 |
| Ex. 38 | TTCP | $HNO_3$ | −1.53 | No | |
| Ex. 39 | TTCP | $HNO_3$ | −0.83 | No | 33/28.5 |
| Ex. 40 | TTCP | $HNO_3$ | 0 | No | 27.5/22.0 |
| Ex. 41 | TTCP | $HNO_3$ | 2 | No | 20.5/16.0 |
| Ex. 42 | TTCP | $K_2HPO_4$ | 8.76 | No | 9.0/7.5 |
| Ex. 43 | TTCP | $(NH_4)_2HPO_4$ | 7.96 | No | 8.5/6.5 |
| Ex. 44 | TTCP | $CH_3COOH$ | | No | 4.5/3.5 |
| Ex. 45 | TTCP | NaOH | 13.57 | No | 52/30 |

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

4. The method of claim 1, wherein the calcium phosphates, the setting solution and the temperature that the mixture is heated to are selected such that the injectable paste has a working time in the range of 2.5 min to 30 min.

5. The method of claim 1, wherein the CPC powder comprises one or more of $Ca_4(PO_4)_2O$, $CaHPO_4 \cdot 2H_2O$, CaHPO$_4$, Ca$_8$H$_2$(PO$_4$)$_6$•5H$_2$O, alpha-Ca$_3$(PO$_4$)$_2$, beta-Ca$_3$(PO$_4$)$_2$, Ca$_2$P$_2$O$_7$, Ca$_2$H$_2$P$_2$O$_8$.

6. The method of claim 1, wherein the CPC powder comprises a mixture of Ca$_4$(PO$_4$)$_2$O and CaHPO$_4$.

7. The method of claim 1, wherein the wetting solution is an acidic solution, basic solution, a phosphate-containing solution, an organic solvent, or water.

8. The method of claim 1, wherein the organic solvent is ethanol.

9. The method of claim 1, wherein the wetting solution is an acidic aqueous solution comprising one or more of nitric acid (HNO$_3$), hydrochloric acid (HCl), phosphoric acid (H$_3$PO$_4$), carbonic acid (H$_2$CO$_3$), sodium dihydrogen phosphate (NaH$_2$PO$_4$), sodium dihydrogen phosphate monohydrate, sodium dihydrogen phosphate dihydrate, potassium dihydrogen phosphate (KH$_2$PO$_4$), ammonium dihydrogen phosphate (NH$_4$H$_2$PO$_4$), malic acid, acetic acid, lactic acid, citric acid, malonic acid, succinic acid, glutaric acid, tartaric acid, and oxalic acid.

10. The method of claim 1, wherein the wetting solution is a basic aqueous solution comprising one or more of ammonia, ammonium hydroxide, alkali metal hydroxide, alkali earth hydroxide, disodium hydrogen phosphate (Na$_2$HPO$_4$), disodium hydrogen phosphate dodecahydrate, disodium hydrogen phosphate heptahydrate, sodium phosphate dodecahydrate (Na$_3$PO$_4$•12H$_2$O), dipotassium hydrogen phosphate (K$_2$HPO$_4$), potassium phosphate tribasic (K$_3$PO$_4$), diammonium hydrogen phosphate ((NH$_4$)$_2$HPO$_4$), ammonium phosphate trihydrate ((NH$_4$)$_3$PO$_4$.3H$_2$O), sodium bicarbonate (NaHCO$_3$).

11. The method of claim 1, wherein the ratio of CPC powder to wetting solution in the mixture is less than 10 mg/ml.

12. The method of claim 1, wherein the calcium phosphate powder further comprises at least one additive selected from the group of sodium phosphate (Na$_3$PO$_4$), disodium hydrogen phosphate (Na$_2$HPO$_4$), sodium dihydrogen phosphate (NaH$_2$PO$_4$), disodium hydrogen phosphate dodecahydrate (Na$_2$HPO$_4$•12H$_2$O), disodium hydrogen phosphate heptahydrate (Na$_2$HPO$_4$•7H$_2$O), sodium phosphate dodecahydrate (Na$_3$PO$_4$•12H$_2$O), orthophosphoric acid (H$_3$PO$_4$), calcium sulfate (CaSO$_4$), Ca$_4$(PO$_4$)$_2$O, CaHPO$_4$•2H$_2$O, CaHPO$_4$, Ca$_8$H$_2$(PO$_4$)$_6$•5H$_2$O, alpha-Ca$_3$(PO$_4$)$_2$, beta-Ca$_3$(PO$_4$)$_2$, Ca$_2$P$_2$O$_7$, and Ca$_2$H$_2$P$_2$O$_8$.

13. The method of claim 1, wherein the Ca/P molar ratio of the calcium phosphate powder is in the range of about 0.5 to 2.5.

14. The method of claim 1, wherein the Ca/P molar ratio of the calcium phosphate powder is in the range of about 1.0 to about 2.0.

15. The method of claim 1, wherein the temperature that the mixture is heated to is selected such that the injectable paste has a working time in the range of 6.5 minutes to 24 min.

16. The method of claim 1, wherein the setting solution is an acidic aqueous solution, a basic aqueous solution, or substantially pure water.

17. The method of claim 1, wherein the setting solution is an acidic aqueous solution comprising one or more of nitric acid (HNO3), hydrochloric acid (HCl), phosphoric acid (H$_3$PO$_4$), carbonic acid (H$_2$CO$_3$), sodium dihydrogen phosphate (NaH$_2$PO$_4$), sodium dihydrogen phosphate monohydrate, sodium dihydrogen phosphate dihydrate, potassium dihydrogen phosphate (KH$_2$PO$_4$), ammonium dihydrogen phosphate (NH$_4$H$_2$PO$_4$ malic acid, acetic acid, lactic acid, citric acid, malonic acid, succinic acid, glutaric acid, tartaric acid, and oxalic acid.

18. The method of claim 1, wherein the setting solution is a basic aqueous solution comprising one or more of ammonia, ammonium hydroxide, alkali metal hydroxide, alkali earth hydroxide, disodium hydrogen phosphate (Na$_2$HPO$_4$), disodium hydrogen phosphate dodecahydrate, disodium hydrogen phosphate heptahydrate, sodium phosphate dodecahydrate (Na$_3$PO$_4$•12H$_2$O), dipotassium hydrogen phosphate (K$_2$HPO$_4$), potassium phosphate tribasic (K$_3$PO$_4$), diammonium hydrogen phosphate ((NH$_4$)$_2$HPO$_4$), ammonium phosphate trihydrate ((NH$_4$)$_3$PO$_4$•3H$_2$O), and sodium bicarbonate (NaHCO$_3$).

* * * * *